United States Patent [19]

Krupp et al.

[11] Patent Number: 4,798,835
[45] Date of Patent: Jan. 17, 1989

[54] DL-5-[(2-BENZYL-3,4-DIHYDRO-2H-BENZO-PYRAN-6-YL)METHYL]THIAZOLIDINE-2,4-DIONE AS AN ANTI-ATHEROSCLEROSIS AGENT

[75] Inventors: Michael N. Krupp, Old Saybrook; Archie C. Swindell, Groton, both of Conn.

[73] Assignee: Pfizer Inc., New York, N.Y.

[21] Appl. No.: 127,858

[22] Filed: Dec. 2, 1987

[51] Int. Cl.⁴ ............................................ A61K 31/425
[52] U.S. Cl. ...................................... 514/369; 514/365
[58] Field of Search ................................ 514/365, 369

[56] References Cited

U.S. PATENT DOCUMENTS

| | | | |
|---|---|---|---|
| 4,287,200 | 9/1981 | Kawamatsu et al. | 424/270 |
| 4,340,605 | 7/1982 | Kawamatsu et al. | 424/263 |
| 4,438,141 | 3/1984 | Kawamatsu et al. | 424/248 |
| 4,444,779 | 4/1984 | Kawamatsu et al. | 424/263 |
| 4,461,902 | 7/1984 | Kawamatsu et al. | 548/183 |
| 4,572,912 | 2/1986 | Yoshioka et al. | 514/369 |
| 4,617,312 | 10/1986 | Schnur | 514/369 |
| 4,687,777 | 8/1987 | Meguro et al. | 514/342 |
| 4,703,052 | 10/1987 | Eggler et al. | 514/337 |

*Primary Examiner*—Jerome D. Goldberg
*Assistant Examiner*—Richard Kearse
*Attorney, Agent, or Firm*—Peter C. Richardson; J. Trevor Lumb; Gregg C. Benson

[57] ABSTRACT

This invention relates of the use of a certain thiazolidine-2,4-dione, namely, dl-5-[(2-benzyl-3,4-dihydro-2H-benzopyran-6-yl)methyl]thiazolidine-2,4-dione, or a pharmaceutically acceptable cationic salt thereof, for retarding the development of arterial disease in mammals. More specifically, it relates to a method for reducing the serum cholesterol levels in mammals by administering to said mammals dl-5-[(2-benzyl-3,4-dihydro-2H-benzopyran-6-yl)methyl]-thiazolidine-2,4-dione or a pharmaceutically acceptable cationic salt thereof.

5 Claims, No Drawings

DL-5-[(2-BENZYL-3,4-DIHYDRO-2H-BENZOPYRAN-6-YL)METHYL]THIAZOLIDINE-2,4-DIONE AS AN ANTI-ATHEROSCLEROSIS AGENT

BACKGROUND OF THE INVENTION

1. Field of the Invention

This invention relates of the use of a certain thiazolidine-2,4-dione, namely, dl-5-[(2-benzyl-3,4-dihydro-2H-benzopyran-6-yl)methyl]thiazolidine-2,4-dione, of the formula

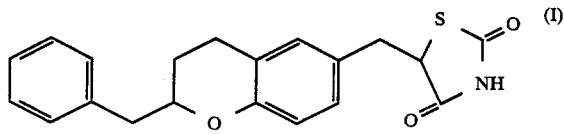

or a pharmaceutically acceptable cationic salt thereof, for retarding the development of arterial disease in mammals. More specifically, it relates to a method for reducing the serum cholesterol levels in mammals by administering to said mammals a compound of formula I or a pharmaceutically acceptable cationic salt thereof.

2. General Background

Atherosclerosis, a disease of the arteries, is recognized to be the leading cause of death in the United States and Western Europe. The pathological sequence leading to atherosclerosis and occlusive heart disease has been described in detail by Ross and Glomset in New England Journal of Medicine 295, 369–377 (1976). The earliest stage in this sequence is the formation of "fatty streaks" in the carotid, coronary and cerebral arteries and in the aorta. These lesions are yellow in color due to the presence of lipid deposits found principally within smooth-muscle cells and in macrophages of the intima layer of the arteries and aorta. Cholesterol and cholesteryl ester account for most of this lipid. Further, it is postulated that most of the cholesterol found within the fatty streaks results from uptake from the plasma. These fatty streaks, in turn, give rise to development of the "fibrous plaque", which consists of accumulated intimal smooth muscle cells laden with lipid and surrounded by extra cellular lipid, collagen, elastin and proteoglycans. The cells plus matrix form a fibrous cap that covers a deeper deposit of cell debris and more extracellular lipid. The lipid is primarily free and esterified cholesterol. The fibrous plaque forms slowly, and is likely in time to become calcified and necrotic, advancing to the "complicated lesion" which accounts for the the arterial occlusion and tendency toward mural thrombosis and arterial muscular spasm that characterize advanced atherosclerosis.

Epidemiological evidence has firmly established hyperlipidemia as a primary risk factor in causing cardiovascular disease (CVD) due to atherosclerosis. In recent years, leaders of the medical profession have placed renewed emphasis on lowering plasma cholesterol levels, and low density lipoprotein cholesterol in particular, as an essential step in prevention of CVD. The upper limits of "normal" are now known to be significantly lower than heretofore appreciated. As a result, large segments of Western populations are now realized to be at high risk for development or progression of CVD because of this factor. Individuals who possess independent risk factors in addition to hyperlipidemia are at particularly high risk. Such independent risk factors include glucose intolerance, left ventricular hypertrophy, hypertension, and being of the male sex. Cardiovascular disease is especially prevalent among diabetic subjects, at least in part because of the existence of multiple independent risk factors. Successful treatment of hyperlipidemia in the general population, and in diabetic subjects in particular, is therefore of exceptional medical importance.

The first step in recommended therapeutic regimens for hyperlipidemia is dietary intervention. While diet alone produces adequate response in some individuals, many others remain at high risk and must be treated further by pharmacological means. New drugs for the treatment of hyperlipidemia are, therefore, of great potential benefit for large numbers of individuals at high risk of developing CVD. Further, successful treatment of both the hyperlipidemia and hyperglycemia associated with the diabetic state with a single therapeutic agent is particularly desirable.

The thiazolidine-2,4-dione of formula I above, among others, is disclosed in U.S. Pat. No. 4,703,052 wherein it is taught that such a compound and its pharmaceutically acceptable cationic salts are useful as hypoglycemic agents, capable of lowering blood glucose levels in mammals. That patent also discloses how to prepare such compounds. However, in spite of the above-mentioned use for the thiazolidine-2,4-dione of formula I as a hypoglycemic agent, there was, prior to the time of the present invention, no report of the use or intent to use such a compound or its salts for lowering serum cholesterol levels nor any appreciation of its role in achieving that desirable effect.

Certain 5RS racemic and 5R optically active oxazolidine-2-one compounds of the formula

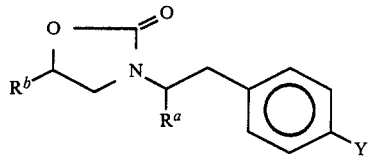

wherein
$R^b$ is

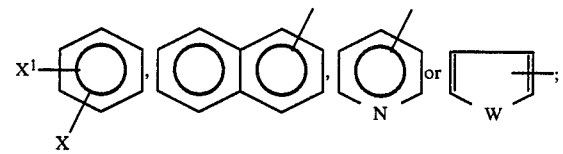

W is sulfur or oxygen;
X and $X^1$ are each independently H, Cl, F or $CF_3$;
Y is inter alia

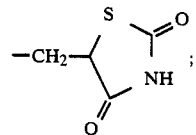

and certain pharmaceutically acceptable salts thereof are disclosed in international patent application number PCT/US87/01356 which is assigned to and has been filed in the name of the assignee thereof. That patent application also discloses the use of such compounds as hypoglycemic agents and, further, the use of some, if not all, of such compounds to lower blood cholesterol levels.

SUMMARY OF THE INVENTION

It has now been found that dl-5-[(2-benzyl-3,4-dihydro-2H-benzopyran-6-yl)methyl]thiazolidine-2,4-dione of the formula

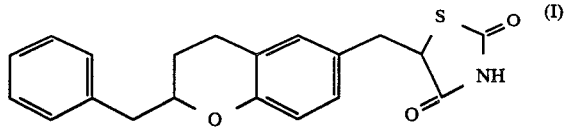

or a pharmaceutically acceptable cationic salt thereof, when administered to a mammal, produces a direct therapeutic benefit in lowering the serum cholesterol level in said mammal.

Mixtures of optically active isomers and partially or completely optically resolved isomers of the compound of formula (I) are within the scope of the present invention.

The high incidence of atherosclerosis in the United States, noted above, gives rise to normotensive individuals, free of congestive heart disease and/or ischemic heart disease, problems normally considered as cardiac complications of hypertension. Still further, cardiovascular disease is a leading cause of death among diabetics. The ability to lower blood cholesterol levels and thereby effect treatment for such cardiovascular disease as atherosclerosis is both desirable and advantageous. The direct therapeutic effect of the thiazolidine-2,4-dione of formula I and its above-mentioned cationic salts in lowering the serum cholesterol levels in such individuals occurs at clinically relevant levels.

The compound of formula (I) contains an asymmetric center at the 2-position and an asymmetric center at the 5-carbon of the thiazolidinedione group. Among the enantiomers of a given compound, one will ordinarily be favored over the others and the racemates because of its greater activity. The present invention is considered to be embracive of the racemates, diastereomeric mixtures, the pure enantiomers and diastereomers of the compound of formula (I), the utility of which is determined by the biological evaluations described below.

DETAILED DESCRIPTION OF THE INVENTION dl-5-[(2-Benzyl-3,4-dihydro-2H-benzopyran-6-yl)methyl]thiazolidine-2,4-dione of the formula

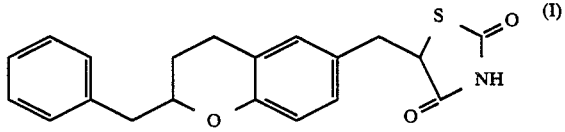

and its pharmaceutically acceptable cationic salts are described in U.S. Pat. No. 4,703,052.

The present invention embraces the pharmaceutically acceptable cationic salts of the compound of formula I by which it is intended to mean salts such as alkali metal salts, (e.g. sodium and potassium), alkaline earth metal salts (e.g. calcium and magnesium), aluminum salts, ammonium salts, and salts with organic amines such as benzathine (N,N'-dibenzylethylenediamine), choline, diethanolamine, ethylenediamine, meglumine (N-methylglucamine), benethamine (N-benzylphenethylamine), diethylamine, piperazine, tromethamine (2-amino-2-hydroxymethyl-1,3-propanediol), procaine, etc. An especially preferred salt is the sodium salt.

The thiazolidine-2,4-dione of the present invention is clinically administered to mammals, including man, via either the oral or the parenteral route. Administration by the oral route is preferred, being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 0.10 to about 50 mg/kg body weight of the subject per day, preferably about 0.10 to about 10 mg/kg body weight per day administered singly or as a divided dose. However, the optimum dosage for the individual subject being treated will be determined by the person responsible for treatment, generally smaller doses being administered initially and thereafter increments made to determine the most suitable dosage. This will vary according to the particular compound/salt employed and with the subject being treated.

The compound of the present invention can be used in pharmaceutical preparations containing the compound, or a pharmaceutically acceptable cationic salt thereof, in combination with a pharmaceutically acceptable carrier or diluent. Suitable pharmaceutically acceptable carriers include inert solid fillers or diluents and sterile aqueous or organic solutions. The active compound will be present in such pharmaceutical compositions in amounts sufficient to provide the desired dosage amount in the range described above. Thus, for oral administration the compounds can be combined with a suitable solid or liquid carrier or diluent to form capsules, tablets, powders, syrups, solutions, suspensions and the like. The pharmaceutical compositions may, if desired, contain additional components such as flavorants, sweeteners, excipients and the like. For parenteral administration the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically acceptable cationic salts of the compounds. The injectable solutions prepared in this manner can then be administered intravenously, intraperitoneally, subcutaneously, or intramuscularly, with intramuscular administration being preferred in man.

The studies described below demonstrate that the compound of formula I, above, effects the lowering of serum cholesterol levels in mammals. The sodium salt of the compound of formula I as a mixture of optically active isomers was used in all the studies.

In one study, female mice (strain C57Br/cd J), obtained from Jackson Laboratories, Bar Harbor, Maine, were used at age 8–12 weeks, following 2–4 weeks acclimation having free access to water and standard laboratory chow. Animals were divided randomly into three groups of 6–7 animals. All three groups were placed on a diet containing 0.75% cholesterol, 31% sucrose, 15.5% starch, 20% casein, 17% cellulose, 4.5% corn oil, 5% coconut oil, 0.25% cholic acid, 4% salts and 2% vitamin; permitted to feed ad lib for 10 days; and dosed daily at 9–11 a.m. for the final 5 days by oral gavage, the control group with 5 ml/kg of vehicle (0.1% aqueous methyl cellulose) and the test groups with the compound under study at 6 mg/kg/day or 20 mg/kg/day in vehicle. After the fourth day of dosing, the animals were fasted overnight, starting at 5 p.m. The following morning a fifth and final dose of the compound was administered to the test groups and, three hours later, the animals were sacrificed by decapitation. Blood from the body trunk was collected and allowed to clot, and the serum assayed enzymatically, using an Abbott VP automated analyzer, for HDL cholesterol, LDL and VLDL cholesterol, and total cholesterol, with the results shown in Table I, below.

TABLE I

|  | LDL + VLDL Cholesterol (mg/dl) | HDL Cholesterol (mg/dl) | Total Cholesterol (mg/dl) | LDL + VLDL/HDL Ratio |
|---|---|---|---|---|
| Sucrose Plus Cholesterol Diet | 146 | 27.6 | 174 | 5.3 |
| Sucrose Plus Cholesterol Diet With Compound at 6 mg/kg/day | 93 | 24.6 | 117 | 3.8 |
| Sucrose Plus Cholesterol Diet With Compound at 20/mg/kg/day | 91 | 36.8 | 128 | 2.4 |

Whether judged on the basis LDL+VLDL cholesterol levels, total cholesterol levels or the ratio of LDL+VLDL/HDL, the compound of this invention shows a highly favorable result in lowering cholesterol levels.

In another set of studies, adult purebred beagle dogs were obtained from Marshall Farms, North Rose, N.Y., and acclimated for several weeks. The dogs were divided into experimental groups in order to perform the following studies. In one study, there were four groups of animals consisting of one animal per sex in each group. Three groups were given the compound under study orally at dose levels of 5, 15 and 50 mg/kg/day for a period of two weeks. The vehicle used in this study for the compound was 0.1% aqueous methyl cellulose. In another study, three groups of animals were formed. Two groups were composed of five animals/sex/group and a third group consisted of two animals/sex/group and served as controls. All of the treated animals in the second study received the compound under study orally at a dose of 50 mg/kg/day. The vehicle used in the second study for the compound was 0.5% aqueous methyl cellulose. The first group in this study received the compound for approximately three weeks and the second group received the compound for a period of nine weeks. Control animals in both studies received only vehicle (0.1% aqueous methyl cellulose in the first study above and 0.5% aqueous methyl cellulose in the second study above). In addition to obtaining at least two individual cholesterol levels prior to being dosed with the compound, cholesterol levels were measured at regular intervals throughout the dosing periods of all of the above studies by bleeding the dogs and assaying for cholesterol using a procedure based upon that described by Allain, C. C., et al., Clin. Chem. 20, 470 (1974) which was adapted to employ J. T. Baker reagents (J. T. Baker Chemical Co., Phillipsburg, N.J. 08865) and a COBAS-Bio ® Analyser (Roche Analytical Instruments, Nutley, N.J.).

The results of the above studies on serum cholesterol levels in dogs revealed that the compound of this invention reduced the total serum cholesterol level in the dogs so treated. A reduction in total serum cholesterol level was seen at 5, 15 and 50 mg/kg/day doses. Further, following dosing of the dogs for about 3 and 9 weeks at 50 mg/kg/day, administration of the compound was stopped whereupon the serum cholesterol levels promptly returned to normal or above normal levels. The triglyceride levels in the dogs were not affected by the compound.

What is claimed is:

1. A method for lowering serum cholesterol levels in a mammal in need thereof which comprises administering to said mammal a serum cholesterol level lowering amount of a compound of the formula

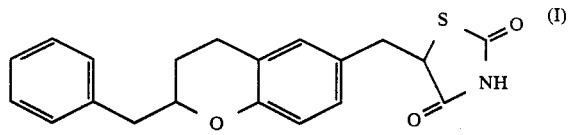

or a pharmaceutically acceptable cationic salt thereof.

2. The method according to claim 1 wherein the compound is administered orally.

3. The method according to claim 2 wherein the compound is the sodium salt of the compound of formula I.

4. The method according to claim 1 wherein the compound is administered parenterally.

5. The method according to claim 4 wherein the compound is the sodium salt of the compound of formula I.